(12) United States Patent
Pfrengle et al.

(10) Patent No.: US 8,101,763 B2
(45) Date of Patent: Jan. 24, 2012

(54) METHOD FOR PRODUCING SCOPINE ESTERS

(75) Inventors: Waldemar Pfrengle, Ingelheim am Rhein (DE); Werner Rall, Ingelheim am Rhein (DE); Joerg Brandenburg, Ingelheim am Rhein (DE); Rolf Herter, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 176 days.

(21) Appl. No.: 12/601,571

(22) PCT Filed: May 9, 2008

(86) PCT No.: PCT/EP2008/055752
§ 371 (c)(1),
(2), (4) Date: Feb. 4, 2010

(87) PCT Pub. No.: WO2008/145504
PCT Pub. Date: Dec. 4, 2008

(65) Prior Publication Data
US 2010/0174067 A1    Jul. 8, 2010

(30) Foreign Application Priority Data
May 25, 2007  (EP) .................................. 07108915

(51) Int. Cl.
C07D 451/10  (2006.01)
C07D 265/36  (2006.01)
(52) U.S. Cl. ......................................... 546/91; 544/105
(58) Field of Classification Search ....................... 546/91
See application file for complete search history.

(56) References Cited

U.S. PATENT DOCUMENTS
7,214,797 B2 * 5/2007 Germeyer et al. ............... 546/91

FOREIGN PATENT DOCUMENTS

| CA | 2417755 A1 | 7/2003 |
|---|---|---|
| CA | 2616222 A1 | 2/2007 |
| CA | 2105575 C1 | 11/2009 |
| WO | 92/16528 A | 10/1992 |
| WO | 03/057694 A | 7/2003 |
| WO | WO 03057694 A1 * | 7/2003 |
| WO | 2007/012626 A | 2/2007 |

OTHER PUBLICATIONS

International Search Report dated Jan. 19, 2009.

* cited by examiner

*Primary Examiner* — Kahsay T Habte
(74) *Attorney, Agent, or Firm* — Michael P. Morris; Wendy A. Petka

(57) ABSTRACT

The invention relates to a novel method for producing scopine esters of the general formula (1), wherein X—, R, R1, R2, R3, R4, R3', R4', R6 and R6' can have the meanings indicated in the claims and in the description.

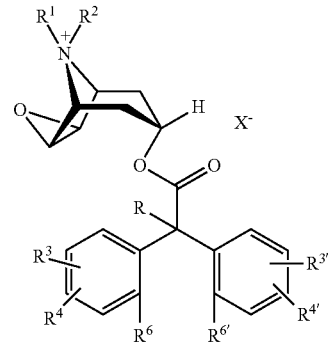

13 Claims, No Drawings

METHOD FOR PRODUCING SCOPINE ESTERS

RELATED APPLICATIONS

This application is a 371 of International Application No. PCT/EP2008/055752, filed May 9, 2008, which claims priority to European Patent Application No 07108915.5, filed May 25, 2007, the contents of which are incorporated herein by reference in their entirety.

The invention relates to a new method for producing scopine esters of general formula 1

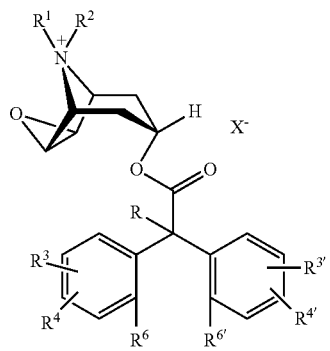

wherein $X^-$ and the groups R, $R^1$, $R^2$, $R^3$, $R^{3'}$, $R^4$ and $R^{4'}$, $R^6$ and $R^{6'}$ may have the meanings given in the claims and specification.

BACKGROUND TO THE INVENTION

Anticholinergics may expediently be used therapeutically in a variety of complaints. Particular mention should be made here, for example, of the treatment of asthma or COPD (chronic obstructive pulmonary disease). For treating these diseases WO 92/16528 proposes for example anticholinergics which have a scopine, tropenol or tropine basic structure. WO 92/16528 also mentions methods of preparing these anticholinergics. Other methods of preparing esters of scopine are disclosed in EP 418 716 A1.

The scopine esters of general formula 1 are already known from WO 03/064419 A1. WO 03/064419 A1 also discloses methods of preparing the scopine esters of general formula 1.

Besides the methods of synthesis disclosed in WO 92/16528 for preparing scopine esters, methods of preparing esters of scopine are also disclosed for example in EP 418 716 A1. The preparation methods known from WO 92/16528 and EP 418 716 A1 and from WO 92/16528 may also be used to prepare the compounds of formula 1. However, these methods of synthesis are in some cases highly complex procedures made up of a number of synthesis steps.

The aim of the present invention is therefore to provide a method of synthesis for preparing the scopine esters according to formula 1, which allows easier synthesis of the compounds of general formula 1, preferably a one-step method of synthesis.

DETAILED DESCRIPTION OF THE INVENTION

Surprisingly it has been found that compounds of formula 1

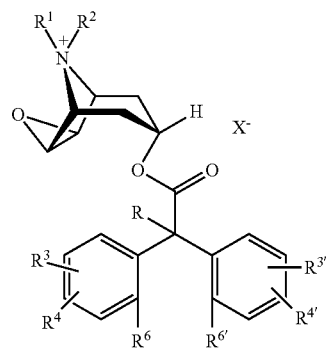

wherein $X^-$ and the groups R, $R^1$, $R^2$, $R^3$, $R^{3'}$, $R^4$, $R^{4'}$, $R^6$ and $R^{6'}$ have the meanings given below, may be obtained in a single reaction step if compounds of formula 2

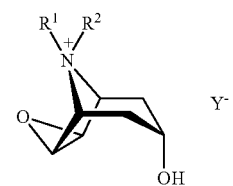

are used as starting material.

Accordingly, the present invention relates to a process for preparing compounds of formula 1

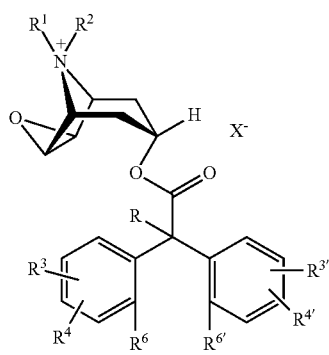

wherein $X^-$ denotes an anion with a single negative charge, preferably an anion selected from among chlorine, bromine, iodine, methanesulphonate or trifluoromethanesulphonate;

R denotes hydrogen, hydroxy, methyl, ethyl, —$CF_3$, $CHF_2$ or fluorine;

$R^1$ and $R^2$ which may be identical or different, denote —$C_1$-$C_5$-alkyl, which may optionally be substituted by —$C_3$-$C_6$-cycloalkyl, hydroxy or halogen, or $R^1$ and $R^2$ together denote a —$C_3$-$C_5$-alkylene bridge;

R³, R⁴, R³' and R⁴', which may be identical or different, denote hydrogen, —C₁-C₄-alkyl, —C₁-C₄-alkyloxy, hydroxy, —CF₃, —CHF₂, CN, NO₂ or halogen, R⁶ and R⁶' denote hydrogen or together represent a single bond, characterised in that a compound of formula 2

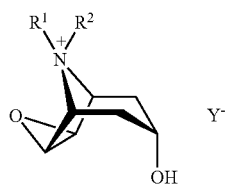

2 wherein

Y⁻ may denote an anion with a single negative charge, preferably chlorine, bromine, iodine, methanesulphonate or trifluoromethanesulphonate, and R¹ and R² may have the meanings given above, is reacted in one step with a compound of formula 3

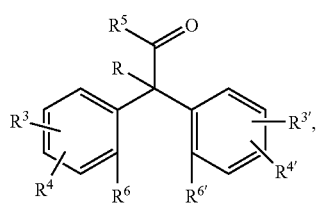

3 wherein

R⁵ denotes a group selected from among hydroxy, methoxy, ethoxy, O—N-succinimide, O—N-phthalimide, phenyloxy, nitrophenyloxy, fluorophenyloxy, pentafluorophenyloxy, vinyloxy, 2-allyloxy, —S-methyl, —S-ethyl and —S-phenyl and wherein R, R³, R³', R⁴, R⁴', R⁶ and R⁶' have the meanings given above.

Preferably the present invention relates to a process for preparing compounds of formula 1

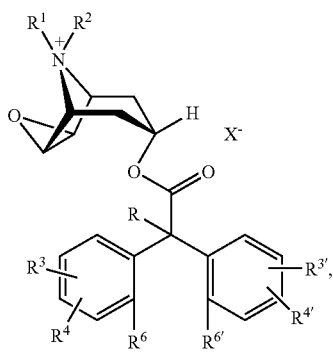

1 wherein

X⁻ denotes an anion selected from among chlorine, bromine, iodine, methanesulphonate or trifluoromethanesulphonate;

R denotes hydroxy, methyl, CF₃ or fluorine

R¹ and R², which may be identical or different, denote methyl or ethyl, preferably methyl R³, R⁴, R³' and R⁴', which may be identical or different, denote hydrogen, —CF₃, —CHF₂ or fluorine, preferably hydrogen or fluorine, wherein R³, R³', R⁴ and R⁴', which may be identical or different, denote hydrogen, methyl, methoxy, hydroxy, —CF₃, —CHF₂ or halogen and R⁶ and R⁶' each denote hydrogen or together represent a single bond, characterised in that a compound of formula 2,

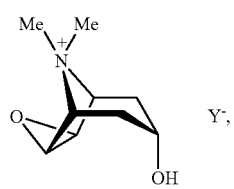

2 wherein

Y⁻ may represent chlorine, bromine, iodine, methanesulphonate or trifluoromethanesulphonate and R¹ and R² may have the meanings given above, is reacted in one step with a compound of formula 3

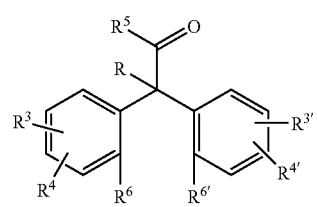

3 wherein

R⁵ denotes a group selected from among hydroxy, methoxy, ethoxy, O—N-succinimide, O—N-phthalimide, phenyloxy, nitrophenyloxy, fluorophenyloxy, pentafluorophenyloxy, vinyloxy, 2-allyloxy, —S-methyl, —S-ethyl and —S-phenyl and R⁶ and R⁶' each denote hydrogen or together represent a single bond and wherein R, R³, R³', R⁴ and R⁴' may have one of the meanings given hereinbefore.

Particularly preferably, the present invention relates to a process for preparing compounds of formula 1

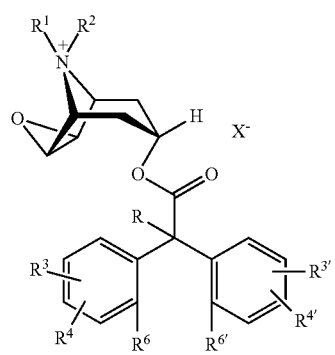

1 wherein

X⁻ denotes bromine, methanesulphonate or trifluoromethanesulphonate;

R denotes hydroxy or methyl $R^1$ and $R^2$, which may be identical or different, denote methyl or ethyl, preferably methyl $R^3$, $R^{3'}$, $R^4$ and $R^{4'}$, which may be identical or different, denote hydrogen, methyl, methoxy, hydroxy, —$CF_3$, or fluorine, preferably hydrogen or fluorine, and $R^6$ and $R^{6'}$ each denote hydrogen or together represent a single bond, characterised in that a compound of formula 2,

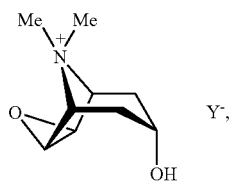

2 wherein $Y^-$ may denote bromine, methanesulphonate or trifluoromethanesulphonate and $R^1$ and $R^2$ may have the meanings given above, is reacted in one step with a compound of formula 3

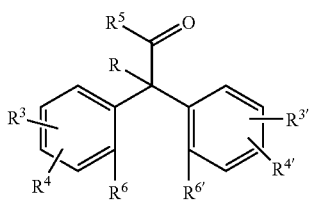

3 wherein $R^5$ denotes a group selected from among hydroxy, O—N-succinimide, O—N-phthalimide, vinyloxy and 2-allyloxy, preferably vinyloxy and 2-allyloxy, and the groups R, $R^3$, $R^4$, $R^{3'}$, $R^{4'}$, $R^6$ and $R^{6'}$ may have one of the meanings given hereinbefore.

In a particularly preferred embodiment the present invention relates to a process for preparing compounds of formula 1

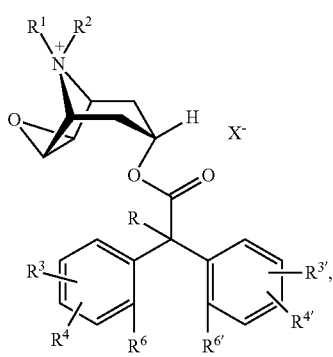

1 wherein $X^-$ denotes an anion with a single negative charge, preferably chlorine, bromine, iodine, methanesulphonate or trifluoromethanesulphonate, particularly bromine;

R denotes methyl, $R^1$ and $R^2$ each denote methyl $R^3$, $R^{3'}$, $R^4$ and $R^{4'}$ each denote hydrogen and $R^6$ and $R^{6'}$ together represent a single bond, characterised in that a compound of formula 2

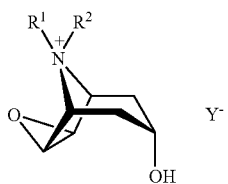

2 wherein $Y^-$ denotes an anion with a single negative charge, preferably chlorine, bromine, iodine, methanesulphonate or trifluoromethanesulphonate, particularly bromine; and $R^1$ and $R^2$ may have the meanings given above, is reacted in one step with a compound of formula 3

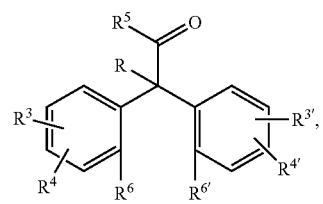

3 wherein $R^5$ denotes a group selected from among hydroxy, methoxy, ethoxy, O—N-succinimide, O—N-phthalimide, phenyloxy, nitrophenyloxy, fluorophenyloxy, pentafluorophenyloxy, vinyloxy, 2-allyloxy, —S-methyl, —S-ethyl and —S-phenyl and the groups R, $R^3$, $R^4$, $R^{3'}$, $R^{4'}$, $R^6$ and $R^{6'}$ have one of the meanings given hereinbefore.

In a particularly preferred embodiment the present invention relates to a process for preparing compounds of formula 1

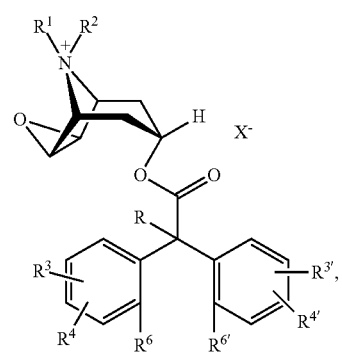

1 wherein $X^-$ denotes an anion with a single negative charge, preferably chlorine, bromine, iodine, methanesulphonate or trifluoromethanesulphonate, particularly bromine;

R denotes methyl,
R¹ and R² each denote methyl and
R³, R⁴, R³' and R⁴' each denote hydrogen and
R⁶ and R⁶' each denote hydrogen,
characterised in that a compound of formula 2

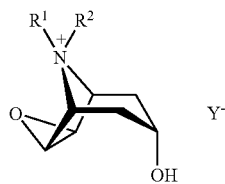

wherein

Y⁻ denotes an anion with a single negative charge, preferably chlorine, bromine, iodine, methanesulphonate or trifluoromethanesulphonate, particularly bromine; and R¹ and R² each denote methyl,
is reacted in one step with a compound of formula 3

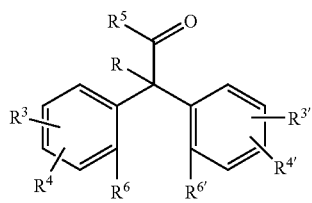

wherein

R⁵ denotes a group selected from among hydroxy, methoxy, ethoxy, O—N-succinimide, O—N-phthalimide, phenyloxy, nitrophenyloxy, fluorophenyloxy, pentafluorophenyloxy, vinyloxy, 2-allyloxy, —S-methyl, —S-ethyl and —S-phenyl and R denotes methyl and
R³, R⁴, R³' and R⁴' each denote hydrogen and
R⁶ and R⁶' each denote hydrogen.

In order to carry out the process according to the invention the following procedure may be used.

In a first step the compound of formula 3 is taken up in a suitable organic solvent, preferably in a polar organic solvent, particularly preferably in a solvent selected from among acetonitrile, nitromethane, formamide, dimethylformamide, N-methylpyrrolidinone, dimethylsulphoxide and dimethylacetamide while of the above-mentioned solvents dimethylformamide, N-methylpyrrolidinone and dimethylacetamide are particularly preferred. Of particular importance according to the invention are dimethylformamide and N-methylpyrrolidinone, the latter being particularly preferred.

Preferably between 0.5 and 2 L, particularly preferably between 0.75 and 1.5 L of the solvent mentioned are used per mol of the compound of formula 3 used.

Depending on the choice of the compound of formula 3 it may optionally be sensible to activate it before reacting it with the compound of formula 2. If derivatives wherein R=hydroxyl are used as the compound of formula 3, for example the use of corresponding activating reagents such as carbonyldiimidazole, carbonyldi-1,2,4-triazole, dicyclohexylcarbodiimide or ethyl-dimethylaminopropylcarbodiimide according to the invention is preferred, while in this connection the use of carbonyldiimidazole is particularly preferred. Between 1 and 2 mol of the coupling reagent are used per mol of compound 3 used wherein R=hydroxy. Preferably, 1 to 1.5 mol of the coupling reagent are used. If the above-mentioned coupling reagents are used, as preferred in the case of R=hydroxy, the reaction mixture then obtained is preferably stirred at a temperature in the range from 15-35° C., preferably 20-25° C. over a period of 1-8 hours, preferably 3-7 hours, before reaction is continued as described below.

The reaction mixture of 3 in the above-mentioned solvent, optionally after the addition of one of the above-mentioned coupling reagents in the case of R=hydroxy, is then adjusted to a temperature below 30° C., preferably to a temperature between −20° C. and 20° C., particularly preferably to a temperature between −10° C. and 5° C. and the compound of formula 2. Based on the compound 3 originally used, stoichiometric quantities of compound of formula 2 may be added. Preferably, according to the invention, 3 is however present in an excess compared with 2. According to the invention between 0.5 and 1 mol, preferably between 0.7 and 0.95 mol, particularly preferably between 0.75 and 0.9 mol of 2 are used per mol of compound 3 used.

The above-mentioned reaction mixture is then mixed with a suitable base dissolved in one of the above-mentioned solvents. Organic or inorganic bases may be used. The organic bases used are preferably alkali metal imidazolides, which may be generated for example in situ from the alkali metals and imidazole or the alkali metal hydrides and imidazole, or alkali metal-tertiary-amylates which are commercially obtainable. The alkali metal imidazolides used are preferably imidazolides of lithium, sodium or potassium, of which sodium or lithium imidazolide are preferred according to the invention. Particularly preferably lithium imidazolide is used. The alkali metal tertiary amylates used are preferably sodium-tert.-amylate and potassium-tert.-amylate, but particularly sodium-tert.-amylate. The inorganic base used is preferably a hydride of lithium, sodium or potassium. Particularly preferably, sodium hydride is used as the inorganic base. Of all the above-mentioned bases it is particularly preferable to use lithium imidazolide.

If compounds of formula 1 in which R denotes hydroxy are to be obtained, instead of the base-catalysed reaction mentioned above, transesterification under milder reaction conditions may also appear advantageous. Zeolites may advantageously be used as catalysts.

If the reaction is carried out with one of the above-mentioned bases, at least stoichiometric quantities of base are used per mol of the compound 2 used. Preferably 1 to 1.5 mol, preferably 1.1 to 1.3 mol of base are used per mol of the compound 2 used. If the base is added in the form of a solution, as is the case particularly with the lithium imidazolide base that is preferred according to the invention and is generated in situ beforehand, the solvent that is already being used to carry out the above-mentioned steps is preferably used for this purpose. Preferably between 0.3 and 1.3 L, particularly preferably between 0.5 and 1 L of the above-mentioned solvent are used per mol of the base used. After the addition of the base has ended, the mixture is stirred at a temperature in the range from 15-35° C., preferably 20-25° C. over a period of 4-48 hours, preferably 8-36 hours.

An acid H—X is added at constant temperature to the suspension thus produced. The choice of acid is governed by the anion X⁻ in the desired end product of general formula 1. In so far as compounds of general formula 1 wherein X⁻ denotes bromide are preferably synthesised within the scope of the present invention, the next procedure is described for preparing the bromide-containing end products of formula 1 that are preferred according to the invention. It is clear to the skilled man that a corresponding procedure involving selecting the appropriate reagent H—X may also be used analogously for preparing compounds wherein X⁻ does not represent bromide.

In order to prepare compounds of formula 1 wherein X⁻=bromide, preferably 2 to 4 mol, preferably 2 to 3 mol, particularly preferably 2.2 to 2.6 mol of hydrogen bromide are added at constant temperature, based on the compound of formula 3 used. The hydrogen bromide used may be either in gaseous form or in the form of preferably saturated solutions. Preferably, according to the invention, the hydrogen bromide is added after being dissolved in glacial acetic acid. Particularly preferably a 33% hydrogen bromide solution in glacial acetic acid is used. After the addition has ended the mixture is stirred at constant temperature, optionally also while cooling with ice (between 0.5 and 6 hours).

Finally the solution obtained is mixed with a non-polar organic solvent, preferably with a solvent selected from among acetone, toluene, n-butylacetate, dichloromethane, diethyl ether, tetrahydrofuran and dioxane, particularly preferably toluene or acetone.

After thorough mixing, the product that has crystallised out is separated off and washed with the above-mentioned non-polar solvent. In order to separate off any water-soluble impurities the crude product may be treated with aqueous bromide solutions, e.g. sodium or potassium bromide solution.

Further purification of the compounds of formula 1 thus obtained may, if necessary, be carried out by chromatography through silica gel or by recrystallisation from suitable solvents such as e.g. water or lower alcohols, such as for example isopropanol.

By using the compounds of formula 2 known in the art as starting materials for synthesising the structures of formula 1 it is possible to obtain these anticholinergically active structures in only one reaction step.

Accordingly, in another aspect, the present invention relates to the use of compounds of formula 2

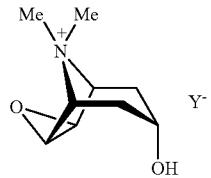

wherein
Y⁻ denotes chlorine, bromine, iodine, methanesulphonate or trifluoromethanesulphonate
as starting material for preparing compounds of formula 1

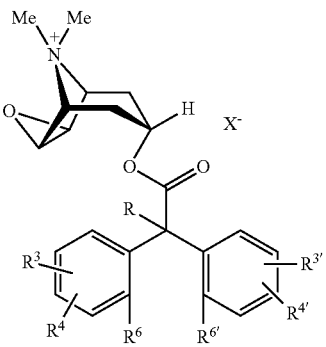

wherein
X⁻ denotes chlorine, bromine, iodine, methanesulphonate or trifluoromethanesulphonate;
R denotes hydroxy, $C_1$-$C_4$-alkyl, $C_1$-$C_4$-alkoxy, $CF_3$ or fluorine and $R^3$, $R^4$, $R^{3'}$ and $R^{4'}$, which may be identical or different, denote hydrogen, —$C_1$-$C_4$-alkyl, —$C_1$-$C_4$-alkyloxy, hydroxy, —$CF_3$, —$CHF_2$, CN, $NO_2$ or halogen and
$R^6$ and $R^{6'}$ each denote hydrogen or together represent a single bond.

Preferably the present invention relates to the use of compounds of formula 2

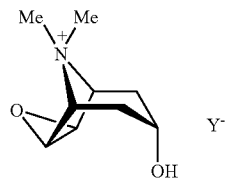

wherein
Y⁻ denotes bromine, methanesulphonate or trifluoromethanesulphonate as starting material for preparing compounds of formula 1

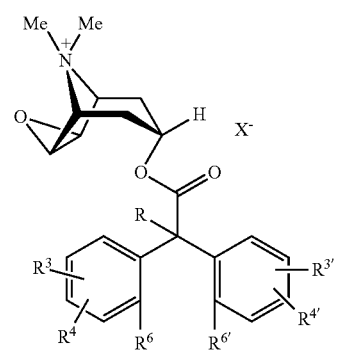

wherein
X⁻ denotes bromine, iodine, methanesulphonate or trifluoromethanesulphonate;
R denotes hydroxy, methyl, $CF_3$ or fluorine and
$R^3$, $R^4$, $R^{3'}$ and $R^{4'}$, which may be identical or different, denote hydrogen, methyl, methoxy, hydroxy, —$CF_3$, —$CHF_2$ or halogen and
$R^6$ and $R^{6'}$ each denote hydrogen or together represent a single bond.

Particularly preferably the present invention relates to the use of compounds of formula 2

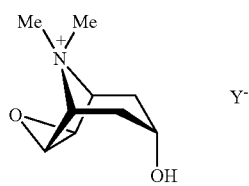

wherein
Y⁻ denotes bromine, methanesulphonate or trifluoromethanesulphonate as starting material for preparing compounds of formula 1

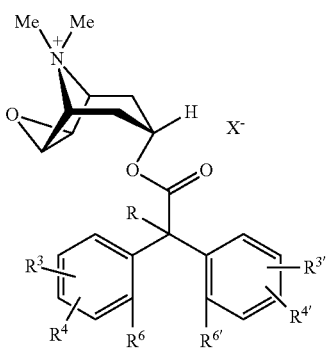

wherein

X⁻ denotes bromine, methanesulphonate or trifluoromethanesulphonate;

R denotes hydroxy or methyl;

$R^3$, $R^4$, $R^{3'}$ and $R^{4'}$, which may be identical or different, denote hydrogen, methyl, methoxy, hydroxy, —$CF_3$ or fluorine and $R^6$ and $R^{6'}$ in each case denote hydrogen or together represent a single bond.

In a particularly preferred embodiment the invention relates to the use of a compound of formula 2

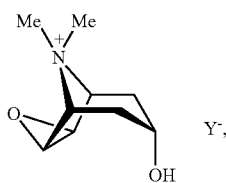

wherein

Y⁻ denotes chlorine, bromine, iodine, methanesulphonate or trifluoromethanesulphonate, as starting material for preparing compounds of formula 1

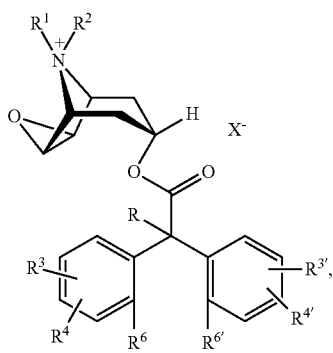

wherein

X⁻ denotes chlorine, bromine, iodine, methanesulphonate or trifluoromethanesulphonate;

R denotes hydroxy, $C_1$-$C_4$-alkyl, $C_1$-$C_4$-alkoxy, $CF_3$ or fluorine; preferably methyl $R^3$, $R^4$, $R^{3'}$ and $R^{4'}$, which may be identical or different, denote hydrogen, —$C_1$-$C_4$-alkyl, —$C_1$-$C_4$-alkyloxy, hydroxy, —$CF_3$, —$CHF_2$, CN, $NO_2$ or halogen, preferably in each case hydrogen, and $R^6$ and $R^{6'}$ together denote a single bond, preferably in the presence of an alkali metal salt of tert.-amylate as base, particularly in the presence of sodium-tert.-amylate as base.

The following Examples serve to illustrate some methods of synthesis carried out by way of example. They are to be construed purely as possible procedures described by way of example without restricting the invention to their contents.

In a particularly preferred embodiment the present invention relates to the use of compounds of formula 2

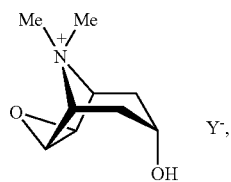

wherein

Y⁻ denotes bromine, as starting material for preparing compounds of formula 1,

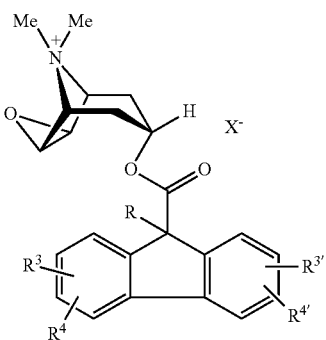

wherein

X⁻ denotes bromine,

R denotes methyl and $R^3$, $R^4$, $R^{3'}$ and $R^{4'}$ denote hydrogen.

Example 1

Scopine 9-methyl-fluorene-9-carboxylate methobromide

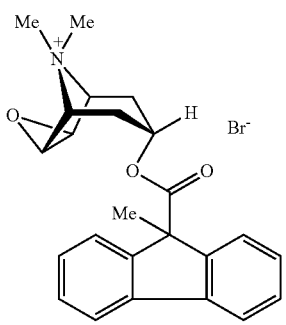

900.0 g (4.013 mol) 9-methyl-fluorene-9-carboxylic acid are added to a solution consisting of 710.8 g (4.384 mol)

1,1-carbonyldiimidazole in 8.43 liters N-methylpyrrolidone and the reaction mixture is stirred for 2.5-3.0 hours at ambient temperature. Then 843.4 g (3.372 mol) scopine methobromide and 408.4 g (3.709 mol) sodium-tert.-amylate are added batchwise. The reaction mixture is heated to 40-45° C. for 3.0-3.5 hours. Then the reactor contents are cooled to 0-3° C. and 1.38 liters HBr, 33% in glacial acetic acid, are slowly added at a temperature of 0-7° C. After the end of the addition, the mixture is stirred for a further 15 minutes and then 9.64 liters of isopropanol are metered in. The suspension is stirred overnight at 0-3° C., filtered, the filter cake is washed with 1.5 liters isopropanol and then dried in vacuo at 45° C. The crude product thus obtained is then dissolved in 7.39 liters of G-water at 60° C. By adding 48% hydrobromic acid the pH of the solution is adjusted to a pH value in the range from 3.0 to 4.0. The solution is filtered clear through activated charcoal, the filtrate is cooled to 0-3° C. during which time the product crystallises out. The suspension thus obtained is stirred for 4-5 hours at 0-3° C., suction filtered, washed with 1.5 liters water and dried at 45° C. in the vacuum dryer.

The following may be obtained analogously in one synthesis step:

Example 2

Scopine 9-fluoro-fluorene-9-carboxylate methobromide

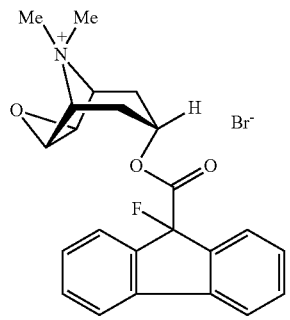

Example 3

Scopine 2,2-diphenylpropionate-methobromide

1. Preparation of: scopine 2,2-diphenylpropionate-methobromide (Crude Product)

10.53 kg (64.97 mol) 1,1-carbonyldiimidazole are dissolved in 101.8 L of N-methylpyrrolidone. At a product temperature of 25° C., 14.70 kg (64.97 mol) of 2,2-diphenylpropionic acid are added batchwise. The reactor contents are stirred for 2 hours at 25° C. and then cooled to 2° C. 12.50 kg (49.79 mol) of BEA 2180 alcohol and 6.54 kg (59.37 mol) of sodium tert.-amylate are added successively at a maximum temperature of 7° C. The funnel is rinsed with 8.9 L N-methylpyrrolidone. The suspension obtained is stirred for 20 minutes at 7° C. The reactor contents are heated to 25° C. and stirred for 5 hours at this temperature. Then 125 L isopropylalcohol are added at 16° C. and the reaction mixture is combined at 16-21° C. with 28.59 kg (116.59 mol) hydrogen bromide 33% in acetic acid. The feed vessel is rinsed with 17.9 L isopropyl alcohol. The suspension is stirred for 14 hours at 23° C. The reactor contents are cooled to 2° C. within 30 minutes and stirred for 3 hours at this temperature. The crude product is centrifuged off, washed twice with 35.7 L isopropylalcohol and dried at 45° C. in the vacuum dryer in vacuo with nitrogen as the entraining gas.

2. Recrystallisation from Isopropanol:

8.00 kg (17.45 mol) of the crude scopine 2,2-diphenylpropionate-methobromide are dissolved in 168 L isopropylalcohol at reflux temperature. After cooling to just below the reflux temperature (79° C.) the mixture is filtered clear through a pressure filter into a 2nd reactor. The pressure filter and the hoses are rinsed with 16 L isopropylalcohol through the 1st reactor. The filtrate in the 2nd reactor is refluxed. After cooling to 70° C. it is seeded with 3.2 g of scopine 2,2-diphenylpropionate-methobromide which has already been recrystallised from isopropanol and the mixture is cooled to 0° C. within 3.5 hours. To complete the crystallisation the mixture is stirred for another 3 hours at 0° C. The suspension is centrifuged off and the product is washed with 32 L of cold isopropylalcohol. The scopine 2,2-diphenylpropionate-methobromide recrystallised from isopropanol is dried at 45° C. in the vacuum dryer, then passed through a 2 mm screen in the shredder.

3. Recrystallisation from Water:

10.00 kg (21.8 mol) of scopine 2,2-diphenylpropionate-methobromide are dissolved in 70 L of G-water at 40° C. The solution is cooled to 25° C. and seeded with 5.0 g of scopine 2,2-diphenylpropionate-methobromide recrystallised from water. Within 30 minutes the mixture is cooled to 20° C. and stirred for 2 hours at this temperature. Within 1 hour the mixture is cooled to 0° C. and stirred for 2.5 hours at this temperature. The suspension is centrifuged off and the product is washed with 20 L of ice-cold G-water. The scopine 2,2-diphenylpropionate-methobromide recrystallised from water is dried at 50° C. in the vacuum drying cupboard.

Depending on the purity of the crude scopine 2,2-diphenylpropionate-methobromide it may be recrystallised either only from isopropanol or from isopropanol and then from water.

The invention claimed is:

1. A process for preparing compounds of formula 1

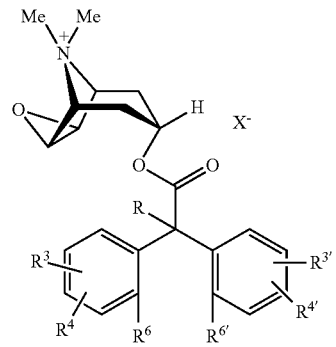

wherein
$X^-$ denotes an anion with a single negative charge,
R denotes hydrogen, hydroxy, methyl, ethyl, —$CF_3$, $CHF_2$ or fluorine;
$R^1$ and $R^2$ which may be identical or different, denote —$C_1$-$C_5$-alkyl, which may optionally be substituted by —$C_3$-$C_6$-cycloalkyl, hydroxy or halogen,
or
$R^1$ and $R^2$ together denote a —$C_3$-$C_5$-alkylene bridge;
$R^3$, $R^4$, $R^{3'}$ and $R^{4'}$, which may be identical or different, denote hydrogen, —$C_1$-$C_4$-alkyl, —$C_1$-$C_4$-alkyloxy, hydroxy, —$CF_3$, —$CHF_2$, CN, $NO_2$ or halogen
$R^6$ and $R^{6'}$ together represent a single bond;

comprising the step of reacting in one step a compound of formula 2

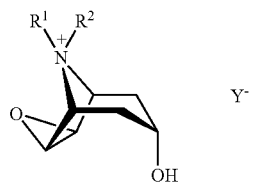

wherein
Y⁻ denotes an anion with a single negative charge, and
R¹ and R² have the meanings given above,
with a compound of formula 3

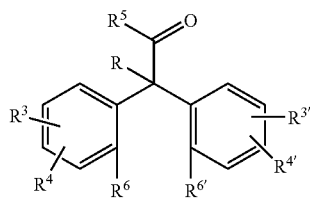

wherein
R⁵ denotes a group selected from among hydroxy, methoxy, ethoxy, O—N-succinimide, O—N-phthalimide, phenyloxy, nitrophenyloxy, fluorophenyloxy, pentafluorophenyloxy, vinyloxy, 2-allyloxy, —S-methyl, —S-ethyl and —S-phenyl and
wherein R, R³, R³', R⁴, R⁴', R⁶ and R⁶' have the meanings given above.

2. Process according to claim 1, for preparing compounds of formula 1,
wherein
X⁻ denotes an anion selected from among chlorine, bromine, iodine, methanesulphonate or trifluoromethanesulphonate
R denotes hydroxy, methyl, CF₃ or fluorine;
R¹ and R² which may be identical or different, denote methyl or ethyl,
R³, R³', R⁴ and R⁴' which may be identical or different, denote hydrogen, methyl, methoxy, hydroxy, —CF₃, —CHF₂ or halogen and
R⁶ and R⁶' together represent a single bond,
characterised in that a compound of formula 2, wherein
Y⁻ may represent chlorine, bromine, iodine, methanesulphonate or trifluoromethanesulphonate
and
the groups R¹ and R² may have one of the meanings given hereinbefore,
is reacted in one step with a compound of formula 3, wherein
R⁵ denotes a group selected from among hydroxy, O—N-succinimide, O—N-phthalimide, vinyloxy and 2-allyloxy,
R⁶ and R⁶' denote hydrogen or together denote a single bond,
and
the groups R, R³, R⁴, R³' and R⁴' may have one of the meanings given hereinbefore.

3. Process according to claim 2 for preparing a compound of formula 1, wherein
X⁻ denotes bromine, methanesulphonate or trifluoromethanesulphonate;
R denotes hydroxy or methyl;
R¹ and R² which may be identical or different, denote methyl or ethyl,
R³, R³', R⁴ and R⁴' which may be identical or different, denote hydrogen, methyl, methoxy, hydroxy, —CF₃ and fluorine, and
R⁶ and R⁶' together represent a single bond,
characterised in that a compound of formula 2, wherein
Y⁻ may represent bromine, methanesulphonate or trifluoromethanesulphonate, and
the groups R¹ and R² may have one of the meanings given hereinbefore,
is reacted in one step with a compound of formula 3, wherein
R⁵ denotes a group selected from among hydroxy, O—N-succinimide, O—N-phthalimide, vinyloxy and 2-allyloxy, and
R⁶ and R⁶' denote hydrogen or together denote a single bond, and
the groups R, R³, R⁴, R³' and R⁴' may have one of the meanings given hereinbefore.

4. Process according to claim 3 for preparing a compound of formula 1, wherein
X⁻ denotes bromine
R denotes methyl;
R¹ and R² each denote methyl
R³, R³', R⁴ and R⁴' each denote hydrogen and
R⁶ and R⁶' together represent a single bond,
characterised in that a compound of formula 2, wherein
Y⁻ denotes bromine and
R¹ and R² each represent methyl is reacted in one step with a compound of formula 3, wherein
R⁵ denotes a group selected from among hydroxy, O—N-succinimide, O—N-phthalimide, vinyloxy and 2-allyloxy,
R denotes methyl and
R³, R⁴, R³' and R⁴' each denote hydrogen and
R⁶ and R⁶' together represent a single bond.

5. Process according to claim 1, wherein the reaction is carried out in an organic solvent selected from among acetonitrile, nitromethane, formamide, dimethylformamide, N-methylpyrrolidinone, dimethylsulphoxide and dimethylacetamide.

6. Process according to claim 1, wherein if a compound of formula 3 having R⁵═OH is used, then activating reagents selected from among carbonyldiimidazole, carbonyldi-1,2,4-triazole, dicyclohexylcarbodiimide and ethyl-dimethylaminopropylcarbodiimide are used.

7. Process according to claim 1, wherein the reaction is carried out at a temperature of less than 30° C.

8. Process according to claim 1, wherein the reaction is carried out in the presence of an organic or inorganic base.

9. Process according to claim 8, wherein the reaction is carried out in the presence of an alkali metal salt of tert-amylate as base.

10. Process according to claim 9, wherein the reaction is carried out in the presence of sodium-tert-amylate as base.

11. Process according to claim 1, characterised in that in the event that R denotes hydroxy in the compounds of formula 1, the reaction is carried out in the presence of zeolites as catalyst.

12. The process according to any one of claims 3-4, wherein R⁵ denotes vinyloxy or 2-allyloxy.

13. The process according to claim 7, wherein the reaction is carried out at a temperature of between −20° C. and 20° C.

* * * * *